United States Patent
Pfefferle

(10) Patent No.: US 7,550,643 B2
(45) Date of Patent: *Jun. 23, 2009

(54) ISOBUTANE ALKYLATION

(75) Inventor: William C. Pfefferle, Madison, CT (US)

(73) Assignee: Precision Combustion, Inc., North Haven, CT (US)

(*) Notice: Subject to any disclaimer, the term of this patent is extended or adjusted under 35 U.S.C. 154(b) by 588 days.

This patent is subject to a terminal disclaimer.

(21) Appl. No.: 11/115,512

(22) Filed: Apr. 27, 2005

(65) Prior Publication Data

US 2005/0245782 A1     Nov. 3, 2005

Related U.S. Application Data

(60) Provisional application No. 60/566,126, filed on Apr. 28, 2004.

(51) Int. Cl.
*C07C 2/54* (2006.01)
*C07C 2/58* (2006.01)

(52) U.S. Cl. .................................. 585/720; 585/722

(58) Field of Classification Search .................. 585/720, 585/722
See application file for complete search history.

(56) References Cited

U.S. PATENT DOCUMENTS

| 3,549,557 | A | * | 12/1970 | Pickert et al. | ................. 502/73 |
| 6,858,770 | B2 | * | 2/2005 | Smith, Jr. et al. | ........... 585/720 |
| 2005/0250972 | A1 | | 11/2005 | Pfefferle | |

* cited by examiner

*Primary Examiner*—Thuan Dinh Dang
(74) *Attorney, Agent, or Firm*—Robert L. Rispoli

(57) ABSTRACT

A method for isobutane alkylation is provided wherein a fixed-bed catalytic alkylation reactor comprises at least one catalytic flow channel. A feed stream comprising a compound to be alkylated admixed with a minor amount of an olefin is introduced into the flow channel wherein the flow channel is of sufficiently long configuration to have a mass-transfer-limiting boundary layer. The feed stream is contacted with a catalyst positioned on an inner surface of the flow channel thereby reacting the compound with the olefin to produce an alkylate product.

3 Claims, 1 Drawing Sheet

ISOBUTANE ALKYLATION

CROSS-REFERENCE TO RELATED APPLICATION

This application claims the benefit of U.S. Provisional Application No. 60/566,126 filed Apr. 28, 2004.

BACKGROUND OF THE INVENTION

1. Field of the Invention

The present invention relates to a method for catalytic isobutane alkylation. More particularly, the present invention is directed to a catalytic isobutane alkylation process that is advantageous for the alkylation of isobutane or benzene, as well as other compounds.

2. Description of the Related Art

Isobutane alkylation by reaction with an olefin is an important refinery process producing a high-octane alkane hydrocarbon product used to produce high-octane gasoline of low aromatic content. Commercial alkylation processes rely on use of either hydrogen fluoride or sulfuric acid catalyst systems. Unfortunately, both systems pose both environmental and safety hazards.

Hydrogen fluoride is an extremely toxic gas and thus even very small leaks are both a potentially lethal hazard for plant personnel and an area-wide health hazard. On the other hand, sulfuric acid is a burn hazard and the organics-contaminated spent acid is a toxic material that, if burned, creates sulfur oxide fumes. Consequently, it is an object of the present invention to provide a more environmentally benign alkylation process that could be used for alkylation of butane and aromatic compounds such as benzene. It is another object of the present invention to provide solid catalyst systems for use in heterogeneous fixed bed reactors.

With the development of synthetic zeolites, solid catalysts with a high activity for isobutane alkylation have become available. As is known in the art, zeolitic catalysts active for commercial alkylation processes also are active for olefin polymerization, a reaction that reduces alkylate octane and can produce high molecular weight polymers. Further, because the olefin polymerization reaction tends to be favored over the desired alkylation reaction, a very high ratio of isobutane-to-olefin must be used to reduce the probability of olefin-to-olefin polymerization.

In commercial alkylation processes, polymer formation produces sludge; however, it is merely a nuisance. In contrast, in an alkylation process employing a solid catalyst, polymer formation can block the active sites thereby requiring catalyst regeneration. Moreover, with both conventional and zeolite catalysts, the required high isobutane-to-olefin ratio increases operating cost because the unreacted isobutane must be recovered from the product stream and recycled. Unfortunately, polymer formation on a fixed-bed zeolitic catalyst results in catalyst deactivation in an economically unacceptable short time if operated at the isobutane-to-olefin ratio used in the commercial processes.

Accordingly, it is an object of the present invention to provide a catalytic isobutane alkylation process that overcomes these and other drawbacks associated with known commercial alkylation processes. It is yet another object of the present invention to provide a catalytic isobutane alkylation process that is advantageous regardless of the compound to be alkylated, most typically isobutane or benzene. The catalytic isobutane alkylation process according to the present invention is described with reference to isobutane.

BRIEF SUMMARY OF THE INVENTION

It has now been found that polymer formation on a fixed-bed alkylation catalyst can be reduced to an acceptable level in order to allow the use of known solid alkylation catalysts at isobutane-to-olefin ratios no higher than the ratios used in commercial isobutane alkylation processes. The present invention allows operation even at isobutane-to-olefin ratios lower than those required in current commercial processes. It has now been found that high isobutane ratios on the catalyst surface do not require high isobutane ratios for the feed streams. Although described in terms of isobutane alkylation, the method of the present invention is generic and applies to alkylation of any compound with an olefin.

The present invention promotes an economically feasible use of fixed bed catalysts. In addition, the present invention offers the potential to reduce the extent of isobutane required to be recycled to a value lower than that of present commercial processes. In accordance with the present invention, a fixed bed alkylation reactor can be operated in a mass-transfer controlled regime for the desired alkylation reaction with the olefin as the limiting reactant, such that the concentration of olefin on the surface will be minimal. The rate of diffusion of olefin to the catalyst surface is maintained sufficiently low such that olefin molecules react with isobutane before encountering another olefin molecule. Thus, the probability of olefin-olefin reaction (polymerization) is greatly reduced by limiting the rate of mass transfer of olefin to the catalyst surface to a value lower than that required for significant polymerization.

Excess olefin arriving at a catalyst surface tends to polymerize. As is known in the art, mass transfer rate to a solid surface is limited by boundary layer thickness. Thus, the rate of mass transfer to a catalytic surface in a flow channel can be controllably limited by choosing flow conditions which increase boundary layer thickness. Accordingly, laminar flow is preferred. Catalyst substrates that maximize mass transfer, such as for example pellet bed and ultra short channel length monolithic catalysts, are disadvantageous with presently known alkylation catalysts.

Catalyst substrates suitable for the present invention include conventional monolith catalysts having flow channel lengths more than long enough for full boundary layer build-up are preferred in the present invention. However, even monolith flow channels can have an entry region where the boundary layer is minimal and the mass transfer rate much too high. Thus, in the present invention it is required for all but the lowest flow velocities that the flow channel entrance region of flow channels be free of catalyst. Further, because olefin polymerization degrades alkylate value and may block catalyst sites, it is desirable that the mass transfer of olefin to the catalyst surface be sufficiently limited such that the olefin concentration on the surface is too low for significant polymerization, preferably even at the initial contact zone.

As is well known in the art, diffusion rate to a surface is determined by boundary layer thickness and the concentration gradient. Thus, the flow velocity and the olefin concentration in the olefin feed stream can be chosen such that the rate of delivery of olefin to the catalyst surface is mass-transfer-limited to a value low enough to minimize polymerization to a desired level. Benzene and other compounds may be alkylated in the method of the present invention.

DETAILED DESCRIPTION OF THE INVENTION

Figure 1:
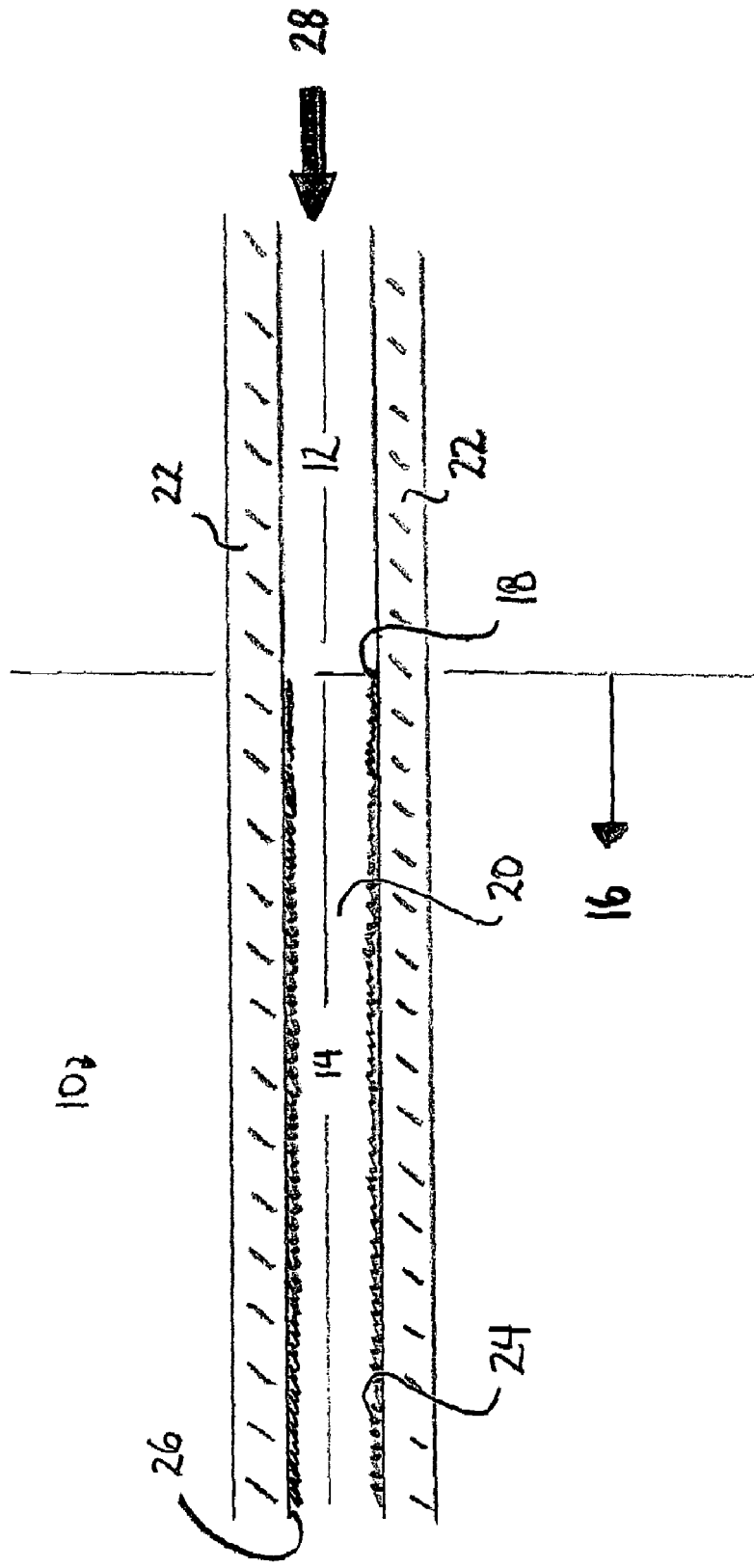
FIG. 1 depicts a diagrammatic section representation of catalytic isobutane alkylation according to the present invention.

As depicted in FIG. 1, the catalytic isobutane alkylation reactor 10 comprises an alkylation reactor flow channel 20 that defines flow channel wall 22. Flow channel 20 further defines entrance region 12 and downstream region 14, wherein downstream flow 16 indicates the direction of flow through the reactor. An alkylation catalyst 24 is positioned on the inner face 26 of channel wall 22 in downstream region 14. The upstream position limit of catalyst 24 defines a transition point 18 between entrance region 12 and downstream region 14. Catalyst 24 may be positioned on only a portion of inner face 26 of channel wall 22, in downstream region 14.

A feed stream 28 comprising olefin and isobutane is introduced into the catalytic reactor 10 passing into entrance region 12. The isobutane flow rate is controlled such that a boundary layer is fully developed in downstream region 14. Catalytic reactor 10 is operated in a mass-transfer controlled regime for the alkylation of the isobutane in feed stream 28. The olefin in feed stream 28 serves as a limiting reactant, such that the concentration of olefin on inner face 26 of channel wall 22 will be minimal.

Although the invention has been described in considerable detail, it will be apparent that the invention is capable of numerous modifications and variations, apparent to those skilled in the art, without departing from the spirit and scope of the invention. For example, although conventional monolith structures make possible compact reactors, reactors comprising individual tubes may be used and make possible longer reactors thereby taking full advantage of the method of the present invention.

What is claimed is:

1. A method of operating a fixed-bed alkylation reactor having at least one catalytic flow channel comprising:
    a) obtaining a feed stream comprising isobutane admixed with an amount of an olefin lower than that required for significant polymerization;
    b) passing the feed stream into the catalytic flow channel wherein the catalytic flow channel defines a mass-transfer-limiting boundary layer limiting the rate of mass transfer of olefin to the catalyst surface to a value lower than that required for significant polymerization;
    c) contacting the feed stream with an alkylation catalyst positioned on the catalyst surface beneath the mass-transfer limiting boundary layer, thereby reacting isobutane with the olefin; and
    d) producing an alkylate product; wherein the catalytic flow channel defining a monolith having an upstream inner surface having no active alkylation catalyst and a downstream inner surface comprising an active alkylation catalyst positioned thereon.

2. The method of claim 1 wherein the reactor comprises a monolith having a plurality of catalytic flow channels of predetermined flow diameter.

3. The method of claim 2 wherein the catalyst comprises a zeolite.

* * * * *